United States Patent
Koninckx

[11] Patent Number: 5,899,851
[45] Date of Patent: May 4, 1999

[54] TV CAMERA WITH ROTATIONAL ORIENTATION CORRECTION

[75] Inventor: Robert Philippe Koninckx, Bierbeek, Belgium

[73] Assignee: Saturnus A.G., Luxembourg, Luxembourg

[21] Appl. No.: 08/591,471

[22] PCT Filed: Jul. 7, 1994

[86] PCT No.: PCT/BE94/00042

§ 371 Date: Apr. 18, 1996

§ 102(e) Date: Apr. 18, 1996

[87] PCT Pub. No.: WO95/01749

PCT Pub. Date: Jan. 19, 1995

[30] Foreign Application Priority Data

Jul. 9, 1993 [NL] Netherlands ............................ 9301210

[51] Int. Cl.[6] ................................................. A61B 1/005
[52] U.S. Cl. ............................ 600/117; 600/103; 600/129
[58] Field of Search .................................... 600/103, 109, 600/112, 117, 137, 145, 173, 129; 348/65, 76; 33/302, 309, 312, 314, 512

[56] References Cited

U.S. PATENT DOCUMENTS

| | | | |
|---|---|---|---|
| 3,525,561 | 8/1970 | Takahashi | 600/103 |
| 3,866,602 | 2/1975 | Furihata | 600/103 |
| 4,277,168 | 7/1981 | Oku | 600/117 |
| 4,359,705 | 11/1982 | Bohn et al. | 335/213 |
| 4,587,741 | 5/1986 | Rorden et al. | . |
| 4,697,210 | 9/1987 | Toyota et al. | 600/109 |
| 4,752,836 | 6/1988 | Blanton et al. | 358/342 |
| 4,850,342 | 7/1989 | Hashiguchi | 600/171 |
| 4,880,011 | 11/1989 | Imade et al. | . |
| 4,885,634 | 12/1989 | Yabe | 600/109 |
| 4,902,129 | 2/1990 | Siegmund et al. | 600/103 |
| 5,224,467 | 7/1993 | Oku | 600/117 |
| 5,280,781 | 1/1994 | Oku | 600/114 |

FOREIGN PATENT DOCUMENTS

| | | |
|---|---|---|
| 0104379 | 4/1984 | European Pat. Off. . |
| 3816982 | 12/1988 | Germany . |
| 4001182 | 7/1990 | Germany . |
| 4102196 | 8/1991 | Germany . |
| 490743 | 3/1992 | Japan .................... 600/109 |
| 620088 | of 1848 | United Kingdom . |

*Primary Examiner*—John P. Leubecker

[57] ABSTRACT

The invention relates to a device for reproducing an image of a poorly accessible location, for example in a living body, comprising a substantially cylindrical image pick-up unit to be arranged at the location and an image display means connected to the image pick-up unit, wherein the image pick-up unit is provided with indication means for indicating the rotation position of the image pick-up unit on its axis relative to the horizontal. As a result of these steps it is possible to give an indication of the horizontal, or for example the vertical, on the image reproduced on the image display means, so that the orientation of the displayed image is known, or by processing the displayed image or by turning the image display means such that the orientation of the displayed image corresponds with the actual orientation. Dangerous situations, for instance during performance of an operation, can herewith be avoided.

19 Claims, 2 Drawing Sheets

TV CAMERA WITH ROTATIONAL ORIENTATION CORRECTION

BACKGROUND OF THE INVENTION

The invention relates to a device for reproducing an image of a poorly accessible location, for example in a living body, comprising a substantially cylindrical image pick-up unit to be arranged at the location and an image display means connected to the image pick-up unit.

Such devices, generally known in for example medical technology, are used for instance to reproduce images from inaccessible places of a living body. Such image pick-up units are herein pushed into the often narrow channels in a body, which channels may for example be formed by veins or arteries or intestines for example, so that the dimensions of such an image pick-up unit have to be very small, for example with a transverse dimension in the order of magnitude of a few millimetres.

SUMMARY OF THE INVENTION

In respect of the usually substantially circular section of such channels such image pick-up units are likewise usually given a cylindrical form. With these cylindrical image pick-up units there is therefore the danger that they will rotate on their axis. When these image pick-up units rotate inside the channel, the image hereby picked up will likewise be transmitted to the image display means rotated relative to the horizontal. When no clear reference to the horizontal is present in the image, as is mostly the case when picking up images inside a body, the orientation of the image reproduced on the image display means is unknown.

BRIEF DESCRIPTION OF THE DRAWINGS

Resulting herefrom is therefore an image for which the transmitted information is incomplete.

When the displayed image is used in performing an operation, dangerous situations can therefore arise. It is thus possible for instance that, as a result of the inaccurate display, an incision which is intended to extend between two intestines extends transversely along the intestines.

In such applications it is known for example to have water drip in front of the camera so that a reference relative to the vertical, and therefore automatically also relative to the horizontal, is obtained. This is awkward however and nothing like possible in all situations.

Attempts are also made, for example with the help of an assistant, to continuously maintain the position of the image pick-up unit on the basis of a known position.

Another typical manner is to reciprocally move an endoscope in which a camera is situated. From the movement on the screen resulting herefrom the deviation of the angle relative to the horizontal can be determined. Correction can take place by rotation of the camera.

The object of the present invention is to provide such a device, wherein the above stated problems are avoided.

This object is achieved in that the image pick-up unit is provided with indication means for indicating the rotation position of the image pick-up unit on its axis relative to the horizontal.

As a result of these steps it is possible to give an indication of the horizontal, or for example the vertical, on the image reproduced on the image display means, so that the orientation of the displayed image is known, or by processing the displayed image or by turning the image display means such that the orientation of the displayed image corresponds with the actual orientation.

Figure 1:
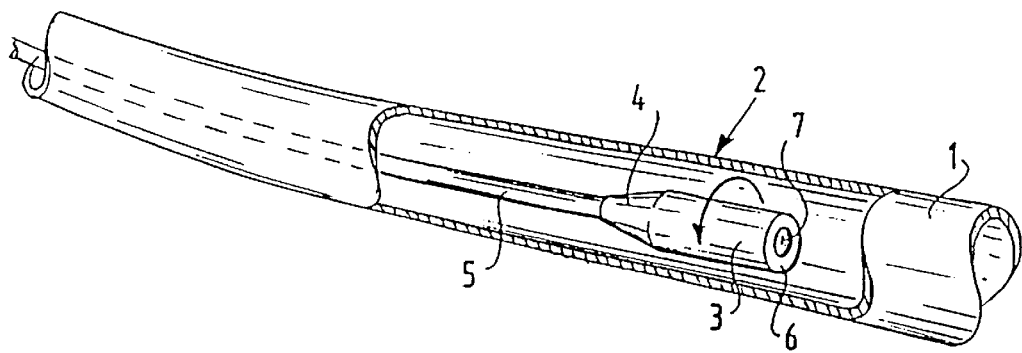
Figure 2:
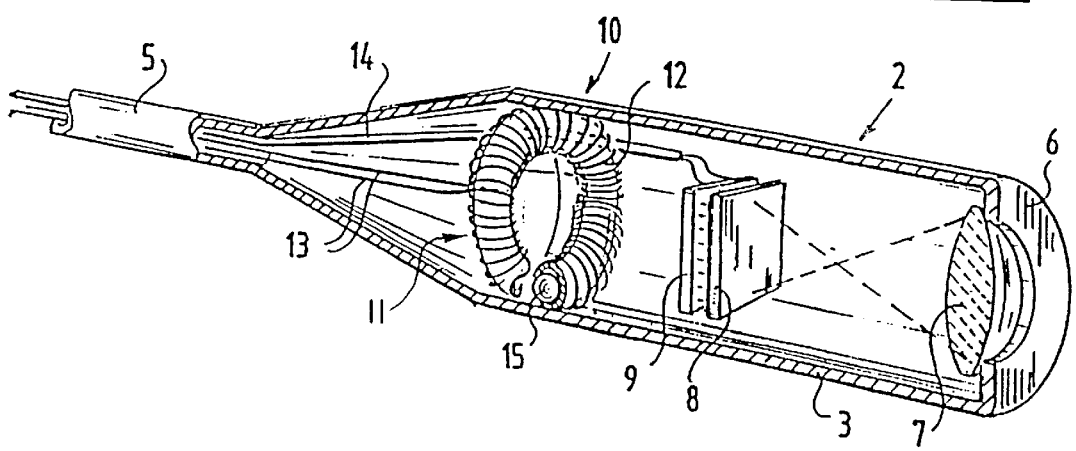
Figure 3:
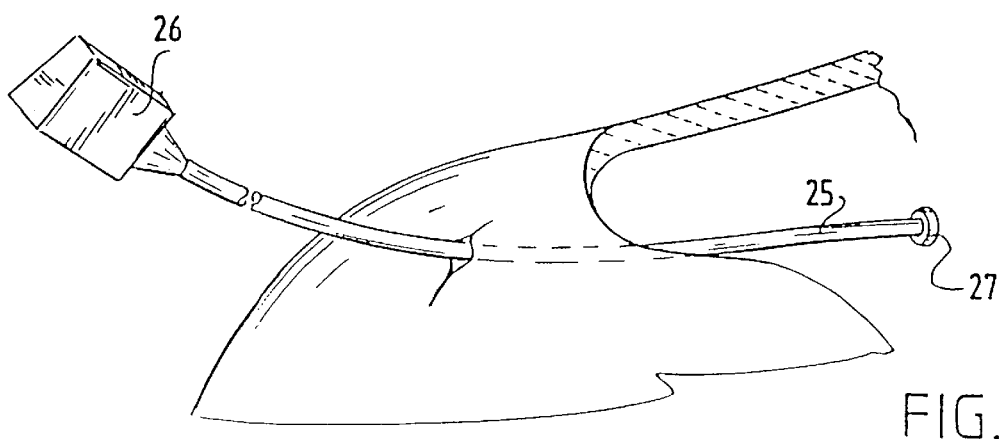
Figure 4:
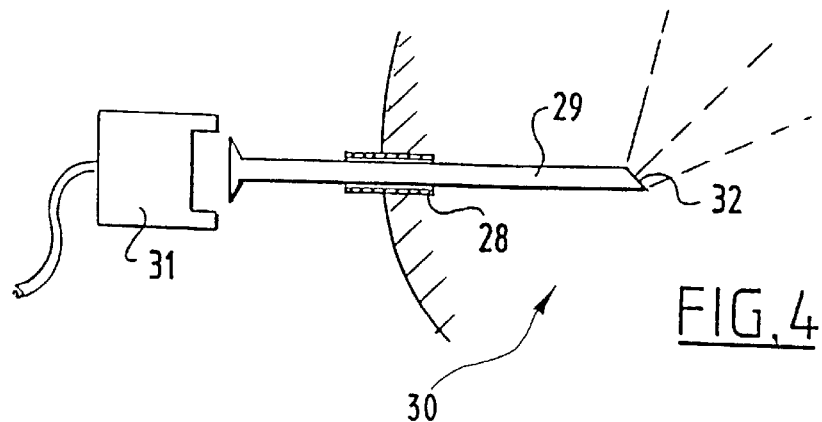
Figure 5:
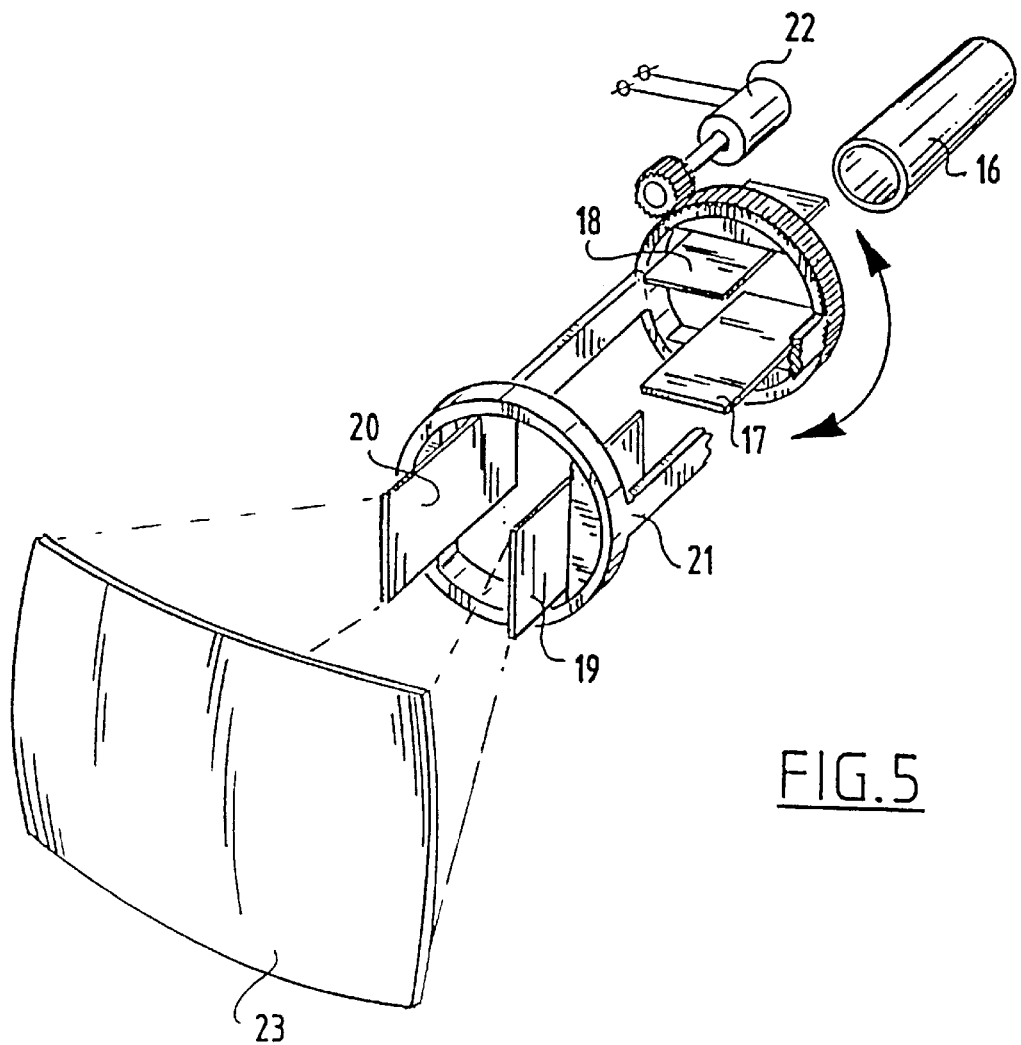

The invention will subsequently be elucidated with reference to the annexed drawings, in which:

FIG. 1 is a partly broken away view of a first embodiment of an image pick-up unit arranged in a channel in the body;

FIG. 2 is a partly broken away enlarged perspective view of the image pick-up unit depicted in FIG. 1;

FIG. 3 shows a second embodiment of an image pick-up unit according to the present invention;

FIG. 4 shows a third embodiment of an image pick-up unit according to the present invention; and FIG. 5 shows an embodiment of a reproducing device which is provided with a correction device according to the invention.

DETAILED DESCRIPTION OF PREFERRED EMBODIMENTS

In the situation depicted in FIG. 1 a channel 1 is shown which is formed for example by a blood vessel in a human body. Situated in channel 1 is an image pick-up unit 2 which is received in a cylindrical housing 3 and which transposes into a cable 5 via a conical part 4. A lens 7 is arranged in the front surface 6 of the image pick-up unit. As a result of the rotation symmetrical form of this image pick-up unit there is a danger that it will rotate inside the channel 1.

The pick-up unit 2 is shown in more detail in FIG. 2. It can be seen here that image pick-up unit 2 is provided with an image pick-up element a in the form of a CCD board which is connected to an electronic circuit 9 located therebehind in which the signal is processed for transmitting thereof via the cable 5 to an image display device placed outside the body.

This image pick-up unit in the form of the shown video camera can of course be equipped with other components of less importance to the present invention, such as a displacing device for the lens in order to enable focussing of the image reproduced on the CCD element 8. In general the lens 7 will therefore be formed by a lens assembly consisting of various elements. A form of diaphragm can also be arranged.

In order to prevent the problems referred to in the preamble a position pick-up means 10 is arranged in the form of a toroidal tube 11 which is made for example of plastic and around which is arranged a winding 12. Arranged in the hollow space of the toroidal tube 11 is a ball 15 which can rotate freely inside the tube and which will always occupy the lowest position as a result of the force of gravity. This position is sensed by the winding which transmits a relevant signal via the cable 13. This is transmitted to the image display device together with the signal representing the image transported via the cable 14. In the image display device such an indication can be given for example by an arrow or a triangle on the top side of the displayed image. The surgeon for instance is thus informed that the displayed image is rotated relative to the horizontal.

It is of course possible to use other forms of rotation pick-up means.

Use is also made of image pick-up units of which the image pick-up surface extends obliquely relative to the rotation axis of the pick-up unit. Herein, when the image pick-up units rotate, the displayed image will not only rotate but also change; the image pick-up units are "looking" the other way.

Before the image is reproduced visually the rotationally uncorrected signal together with the rotational correction signal or the signal corrected using the rotation correction signal can be stored in analog or digital form on a recording medium.

In FIG. 3 another embodiment of an image pick-up unit is shown. This is formed by an optical fiber 25 which leads to a video camera 26. A rotation pick-up means 27 is arranged on the engaging surface of the light conductor 25, so that in this situation rotations of the pick-up means in the form of the optical conductor can also be corrected.

FIG. 4 shows a third embodiment of an image pick-up unit according to the invention. This embodiment is particularly suitable for applications with intra-abdominal endoscopic surgery. A laparoscope 29 is herein introduced into the abdominal cavity 30 by means of a trocar 28. The part of the laparoscope 29 remaining outside the abdominal cavity is situated in the vicinity of a camera 31, wherein it is possible to rotate the laparoscope 29 inside the trocar 28. This is important in the first instance in order to obtain different images from the laparoscope 29. The latter is in any case provided with an oblique pick-up surface 32 that looks away "obliquely". By rotating laparoscope 29 a field of vision can thus be obtained which is formed by a collection of separate images, wherein the central lines of the images form a cone. The field of vision is hereby considerably enlarged compared to a situation where it is only possible to look "straight ahead". Instruments are often carried simultaneously by the same trocar, wherein the operations performed can be viewed carefully using the laparoscope. It should be otherwise noted that the laparoscope can rotate relative to the camera. In these situations a direction indication according to the invention is also of the greatest importance.

It will otherwise be apparent that the camera can also be fixed on the internal end of the laparoscope.

An example of an image display device is shown in FIG. 5. This is formed by a cathode ray tube, the construction of which is assumed known. This cathode ray tube comprises an electrode gun 16, a set of vertical deflecting plates 17, 18, and a set of horizontal deflecting plates 19, 20, which deflecting plates 17–20 are arranged together in a frame 21. This frame is arranged for rotation by means of a servomotor 22. The electron bundle coming from the electron gun 16 falls on a screen 23 and is reproduced there. By thus driving the electric motor 22 with the signal coming from position pick-up means 10 the position of the plates 17–20 is corrected, so that the image reproduced on the display 23 assumes the correct position, and is corrected for rotation of the camera position. It will be apparent that the signal coming from the pick-up unit will have to be amplified before it is fed to the servomotor.

It is likewise possible to rotate the entire picture tube or to process the signal representing the image such that the horizontal in the image is actually displayed horizontally.

I claim:

1. A device for reproducing an image of a poorly accessible location in a living body, said device comprising an image pick-up unit to be arranged at the location, said image pick-up unit comprising:

a signal conduit for receiving and transmitting image information, the signal conduit being configured to at least partially extend into the body;

a torroidal tube and a metal object that moves freely within said torroidal tube in response to gravity, wherein said torroidal tube rotates with said image pick-up unit; and a sensor for sensing a position of said metal object within said torroidal tube and generating a correction signal associated with a rotation position of said image pickup unit;

wherein said torroidal tube defines a central hole, said torroidal tube being arranged such that the image information passes through the central hole; said signal conduit extends into the centralized hole; and said signal conduit comprises an optical fiber.

2. A device as claimed in claim 1, characterized in that the image pick-up unit is adapted to receive light with at least a component along an axial direction of the pick-up unit.

3. A device as claimed in claim 1, including an image display unit configured to receive the image information from the signal conduit and for displaying the image, characterized in that the image display unit is provided with electronic correction means for correcting the rotation position of the image, wherein a signal associated with the correction signal is fed to the correction means.

4. A device as claimed in claim 1, including an image display unit configured to receive the image information from the signal conduit and for displaying the image, characterized in that the image display unit is provided with means for indicating the rotation position on the image.

5. A device as claimed in claim 1 including storage means for storing in a storage medium a signal representing the image.

6. A device as claimed in claim 1, characterized in that the image pick-up unit has an engaging surface which extends at an angle differing from 90° relative to a longitudinal axis of the pick-up unit.

7. The device of claim 1, wherein the metal object comprises a metal ball.

8. The device of claim 1, including an image display unit configured to receive the image information from the signal conduit and for displaying the image, wherein the rotational orientation of the image on the image display unit is corrected by providing a visual indication of the rotation amount on the image display unit.

9. The device according to claim 1, including an image display unit configured to receive the image information from said signal conduit and for displaying the image.

10. The device according to claim 9, wherein said image display unit includes means for correcting a rotation position of the image.

11. The device according to claim 9, wherein said image display unit comprises deflector plates that are rotatable around a stationary axis of the image display unit.

12. The device according to claim 1, wherein said sensor includes windings disposed around said torroidal tube, said windings being configured to sense a position of said metal object within said torroidal tube.

13. A device as claimed in claim 12, including storage means for storing in a storage medium a signal representing the image, characterized in that the storage means is adapted to store the signal representing the image together with a signal associated with the correction signal.

14. A device as claimed in claim 12, including storage means for storing in a storage medium a signal representing the image, characterized in that the storage means is adapted to store the signal representing the image corrected using a signal associated with the correction signal.

15. The device according to claim 1, wherein said image pick-up unit is substantially cylindrical.

16. The device according to claim 1, wherein said optical fiber is connectible to a video camera to be disposed outside the poorly accessible location.

17. A device as claimed in claim 16, characterized in that the device comprises the video camera.

18. A device as claimed in claim 4, characterized in that the image pick-up unit has an engaging surface which extends at an angle differing from 90° relative to a longitudinal axis of the image pick-up unit.

19. A device as claimed in claim 18, characterized in that the image pick-up unit is rotatable around the longitudinal axis.

* * * * *